(12) United States Patent (10) Patent No.: US 8,187,465 B2
Nierich (45) Date of Patent: May 29, 2012

(54) BLOOD RECUPERATION DEVICE AND METHOD

(75) Inventor: Arno Pieter Nierich, Hattem (NL)

(73) Assignee: Gelanus B.V., Hattem (NL)

( * ) Notice: Subject to any disclaimer, the term of this patent is extended or adjusted under 35 U.S.C. 154(b) by 419 days.

(21) Appl. No.: 12/440,288

(22) PCT Filed: Sep. 10, 2007

(86) PCT No.: PCT/EP2007/059450
§ 371 (c)(1),
(2), (4) Date: Mar. 6, 2009

(87) PCT Pub. No.: WO2008/028975
PCT Pub. Date: Mar. 13, 2008

(65) Prior Publication Data
US 2009/0314724 A1 Dec. 24, 2009

(30) Foreign Application Priority Data

Sep. 8, 2006 (EP) .................................. 06120396

(51) Int. Cl.
*B01D 11/00* (2006.01)
*B01D 61/00* (2006.01)
*C02F 9/00* (2006.01)
*A61M 37/00* (2006.01)

(52) U.S. Cl. ............... 210/645; 210/650; 210/416.2; 210/268; 210/263; 604/408; 604/6.09

(58) Field of Classification Search ............ 210/645, 210/650, 261, 195.2, 416.2, 258, 263; 604/403, 604/406, 408, 6.09
See application file for complete search history.

(56) References Cited

U.S. PATENT DOCUMENTS

| 4,014,329 A | 3/1977 | Welch et al. |
| 4,033,345 A | 7/1977 | Sorenson et al. |
| 4,443,220 A | 4/1984 | Hauer et al. |
| 4,631,050 A | 12/1986 | Reed et al. |
| 4,898,572 A | 2/1990 | Surugue |
| 4,976,682 A * | 12/1990 | Lane et al. ............... 604/6.07 |

(Continued)

FOREIGN PATENT DOCUMENTS

DE 3406928 9/1984
(Continued)

OTHER PUBLICATIONS

Official Search Report of the European Patent Office in counterpart foreign application No. PCT/EP2007/059450 filed Sep. 10, 2007.

*Primary Examiner* — Ana Fortuna
(74) *Attorney, Agent, or Firm* — Steven M. Koehler; Westman, Champlin & Kelly, P.A.

(57) ABSTRACT

A blood filtering device for the recuperation of blood from wound drained blood, in particular for an autologous blood transfusion system, has a first filter arranged upstream of a second filter. The first filter is adapted for removing emboli and/or large particulate matter from the blood and for allowing red blood cells to pass. The second filter is adapted for retaining red blood cells. An exit port is arranged downstream of the first filter and upstream of the second filter. The device is characterised in that the second filter has a pore size of more than about 0.5 μm. A method of recuperating blood from wound drained blood is also disclosed.

21 Claims, 8 Drawing Sheets

U.S. PATENT DOCUMENTS

| | | | | |
|---|---|---|---|---|
| 5,055,198 A | * | 10/1991 | Shettigar | 210/650 |
| 5,158,533 A | | 10/1992 | Strauss et al. | |
| 5,215,519 A | * | 6/1993 | Shettigar | 604/6.09 |
| 5,270,005 A | * | 12/1993 | Raible | 422/46 |
| 5,407,425 A | | 4/1995 | Werner et al. | |
| 5,634,893 A | * | 6/1997 | Rishton | 604/6.1 |
| 5,643,193 A | | 7/1997 | Papillon et al. | |
| 5,722,964 A | | 3/1998 | Herweck et al. | |
| 5,772,964 A | * | 6/1998 | Prevost et al. | 422/70 |
| 5,876,611 A | * | 3/1999 | Shettigar | 210/739 |
| 6,996,367 B2 | * | 2/2006 | Pfenninger et al. | 434/362 |
| 7,104,406 B2 | | 9/2006 | Chen et al. | |
| 7,390,484 B2 | * | 6/2008 | Fraser et al. | 424/93.7 |
| 2004/0178129 A1 | * | 9/2004 | Rizzo | 210/130 |
| 2004/0178140 A1 | | 9/2004 | Bell | |
| 2006/0127875 A1 | | 6/2006 | Sukavaneshvar et al. | |

FOREIGN PATENT DOCUMENTS

| | | |
|---|---|---|
| EP | 0205614 | 12/1986 |
| EP | 0518975 | 12/1992 |
| EP | 0594783 | 5/1994 |
| EP | 1457216 | 9/2004 |
| JP | 2000051347 | 2/2000 |
| WO | WO 8602844 | 5/1986 |
| WO | WO 91/13677 | 9/1991 |
| WO | WO 9101367 | 9/1991 |
| WO | WO 93/01858 | 2/1993 |
| WO | WO 2004/105838 | 12/2004 |
| WO | WO 2005/097231 | 10/2005 |

* cited by examiner

BLOOD RECUPERATION DEVICE AND METHOD

CROSS-REFERENCE TO RELATED APPLICATION

The present application is a national stage filing of International patent application Serial No. PCT/EP2007/059450, filed Sep. 10, 2007, and published as WO 2008/028975 in English.

BACKGROUND

The discussion below is merely provided for general background information and is not intended to be used as an aid in determining the scope of the claimed subject matter.

The present disclosure pertains to a blood filtering device and a method for the recuperation of blood from wound drained blood, in particular for an autologous blood transfusion and a system therefor, the filtering device comprising an entrance port for the blood, a first filter and a second filter, wherein the first filter is arranged upstream of the second filter, the first filter adapted for removing emboli and/or large particulate matter from the blood received through the entrance port and for allowing red blood cells to pass, the second filter adapted for retaining red blood cells and an exit port arranged between the first and second filter, i.e. downstream of the first filter and upstream of the second filter.

After a patient has undergone an operation, specific wounds, e.g. thorax wounds after cardiac operations, may be provided with drains to remove the wound secretions, which fluid usually comprises blood. A patient may lose so much blood that he/she requires a blood transfusion. Autologous blood transfusion, the reinfusion of a patients own blood, minimises risks linked to blood transfusions with blood donated by other people, so-called homologous blood transfusions, viz. anaphylactic reactions and/or donor-associated infections such as hepatitis, acquired immune deficiency syndrome (AIDS), adverse effects HLA (human leucocytes antigens), and malaria.

For an autologous blood transfusion, the fluid comprising the lost blood must be collected and the blood to be reinfused must be recuperated therefrom. This blood which preferably is as rich as possible in healthy red blood cells or erythrocytes, must be filtered out of the drained blood and freed or washed from impurities and/or contaminants before reinfusion. Typical impurities in blood drained from a recovering wound site are, among others, bone and tissue fragments, blood clots and fat particles, as well as activated coagulation factors, plasma free haemoglobin, denaturated proteins, platelets, leucocytes and lipids.

The purification of autologous blood, generally called "washing", is usually performed in two steps: first the drained fluid is filtered relatively coarsely to remove large particulate debris and impurities from the blood, next the filtrate is mixed with a "washing fluid", usually a saline solution or Ringer's solution, put in a centrifuge chamber for separation of the relatively heavy blood cells from the blood plasma and relatively light and small particles such as platelets, plasma proteins and antibodies. The recovered blood is generally reinfused under low pressure through a leukocyte filter for further reducing the number of remaining white blood cells in the transfused blood.

This cell washing technique works only for batches. Further, during washing by the centrifuge-process, significant numbers of the collected red blood cells become damaged and are lost to the patient. This method depends on complex equipment that is not available when the blood loss is over an extended period of time, e.g. 6-12 hours, on a non operating room such as an Intensive Care Unit (ICU).

An improvement to this technique is provided by using a two-step filtering system which may be used for continuous or quasi-continuous washing of wound drained blood. Such a filter system is known from EP 0 518 975, which discloses an apparatus for recycling autologous blood from a patient for reinfusion back to the patient comprising suction means, admixing means for admixing aspirated blood with a washing fluid, filtering means for filtering the admixture through an emboli filter and a membrane filter, monitoring means for measuring the amount of cellular component volume in the filtered blood, filtration means for removing excess fluid and particulates from the blood, and reinfusion means. The membrane filter may be any conventional membrane-type separator with a pore-size ranging from 40 000 daltons to 400 000 daltons molecular weight cut-off. However, if larger impurities are to be removed, a plasma filter having a pore size larger than about 400 000 daltons, and up to 0.4 µm, can be used.

In order to achieve filtering of the blood from small impurities through such commercially available membrane filters, experiments have proven that only blood having a blood cellular volume, or haematocrit, of less than about 25% and an applied pressure difference across the membrane filter of more than about 400 mm Hg should be used. Furthermore, the filters tend to clog, requiring an even higher pressure difference and/or an even lower haematocrit for operation. These devices can also work only if strong anticoagulation by medication such as heparin is used during filtering.

It is desired, in particular for severely weakened patients such as those stationed on an intensive care ward, to have a simple, reliable filtering device which may yield purified blood with a high haematocrit value, e.g. 70% or even higher, for autologous blood transfusions. This will enhance recovery of the patient and reduce morbidity and mortality.

Further, systems capable of reaching the necessary relatively high pressure difference, i.e. moderate to high vacuum sources or roller pumps may be unavailable in some hospitals, especially in less-developed countries.

Moreover, it has become apparent that the autologous blood prepared according to the prior art may still comprise impurities such as fractured red blood cells, activated platelets or activated tissue factors, which may cause complications to the patient such as inflammation reactions.

An improved blood filtering device and a method, for the recuperation of blood from wound drained blood is always desired.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the background.

An aspect of the present invention is a blood filter having a second filter that has a pore size of more than about 0.5 µm. Thus, since red blood cells tend to have an average size of about 4 µm and may form small chains or clumps of up to about 10 µm, a filter device according to the present disclosure provides a filtering means to filter out relatively large impurities and to let healthy red blood cells pass through the first filter, whereas the second filter retains these cells and lets fluid and smaller impurities and/or contaminants pass.

The larger pore size of the second filter, compared to the prior art, provides a relatively low fluid flow resistance, so that the device may operate with low or no applied pressure difference across the filter and so that excess fluid, e.g. washing fluid or irrigation fluid, may be filtered out effectively.

Thus a relatively simple device is achieved which provides a filtering window for recuperating red blood cells with minimum additional equipment being necessary.

The pore size of the second filter may be in the range of about 1-10 μm, advantageously in the range of about 2-8 μm, such as in the range of about 4-6 μm, e.g. 5 μm. Selecting a size in this range enables an accurate tuning of the filtering window to retain healthy red blood cells, but to filter out also relatively large impurities.

Such a relatively coarse second filtering step, compared to the prior art, may cause some beneficial factors of the blood to be filtered out and be lost, such as blood platelets. However, most of these platelets are activated and their quantity is mostly low since most will remain in the wound itself in order to reach coagulation at the site of tissue trauma. Thus, the additional reduction of noxious impurities such as other tissue factors and the easy handling of the present device are considered to substantially outweigh this effect, rendering the present filtering device and method a clear improvement over the prior art.

The first filter may have a pore size of less than about 200 μm, or less than about 100 μm, e.g. 50 μm to obtain an efficient filtering action in the first filtering step.

Also provided is a method of recuperating blood from wound drained blood, in particular for an autologous blood transfusion, comprising the steps of aspirating or collecting wound drained blood of a patient in a conduit, filtering the blood from the conduit in a first relatively coarse manner for removing emboli and/or particulate matter from the blood, filtering the coarsely filtered blood in a second relatively fine manner for filtering out small impurities and/or liquid from the blood and retaining red blood cells in the residue, collecting the residue of the second filtering step, the second filtering step being performed to retain particles having a size of more than about 0.5 μm and to remove smaller particles therefrom.

The second filtering step may be performed to filter out and retain particles having a size of more than about 1 μm, advantageously more than about 2 μm, or more than about 4 μm, e.g. about 5 μm, and to remove smaller particles therefrom, and preferably the first, relatively coarse, filtering step is performed to filter out particles having a size of more than about 200 μm, advantageously more than about 100 μm, e.g. more than 50 μm.

The disclosure moreover provides a kit, comprising a blood filtering device as described above, a conduit for draining wound secretions, and a blood receptacle, all packed under sterile conditions, as well as an autologous blood transfusion assembly.

BRIEF DESCRIPTION OF THE DRAWINGS

The device and its operation will become clearer from the following drawings which schematically show non limiting exemplary embodiments.

DETAILED DESCRIPTION OF THE ILLUSTRATIVE EMBODIMENTS

Figure 1:
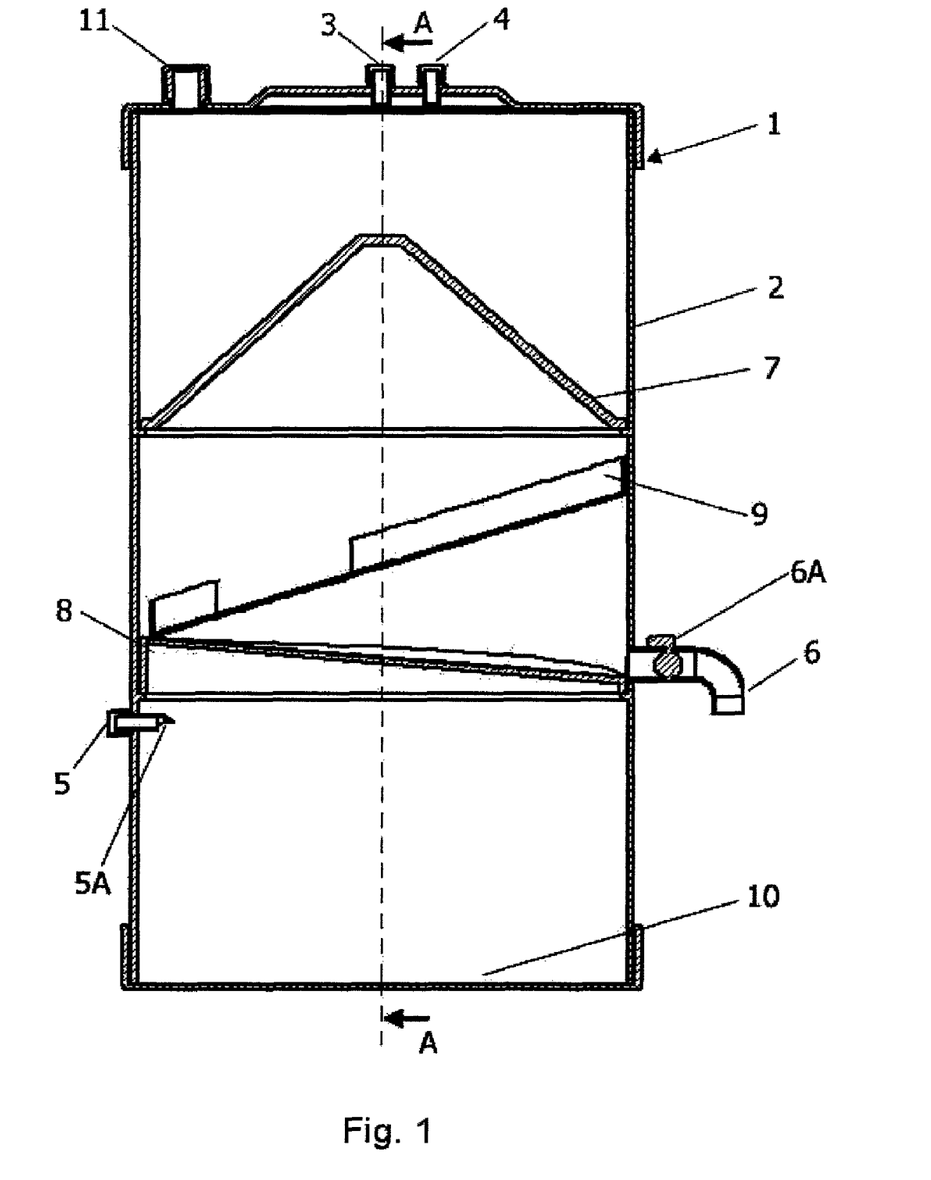
FIG. 1 is a cross sectional view of a blood filtering device for the recuperation of blood from wound drained blood.
Figure 2:
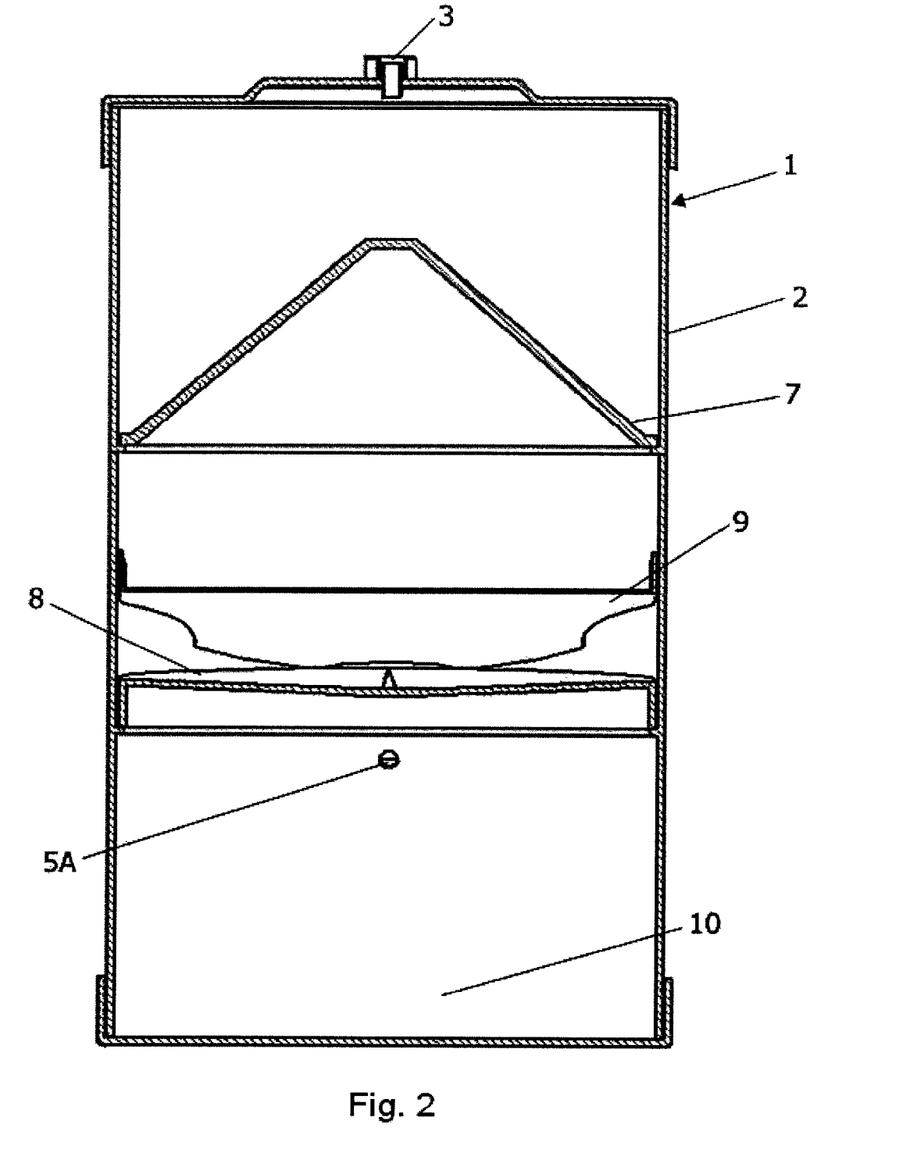
FIG. 2 is a cross sectional view of the blood filtering device perpendicular along the line A-A to the view of FIG. 1.

FIGS. 1 and 2 show a filtering device 1, comprising a generally tubular housing 2, provided with a connection 3 for introducing blood to the device, an optional connection 4 for a source of washing fluid, an optional vacuum connector 5 and an exit port 6 provided with a valve 6A for removing recuperated blood. Inside the housing 2 a first filter 7, a second filter 8 and a baffle 9 are arranged. The housing 2 further comprises a reservoir 10 for waste filtrate and an underpressure safety valve 11. The entrance 5A of the vacuum conduit 5 is oriented away from the second filter to prevent it from aspirating waste filtrate.

The connections 3, 4, 5 and the exit port 6 may be provided with connectors such as standard size Luer Lock connections. Alternatively, the connections may have drains and/or conduits fixedly attached thereto.

The underpressure safety valve 11 may be a microporous hydrophobic filter unit which is capable of passing gasses therethrough but no liquids, but may also be realised differently in any known way.

The filter device 1, a set of drains and conduits and possibly one or more blood receptacles and a quantity of washing fluid may be provided in a single, advantageously sterilely packed, kit which may also comprise appropriate means for application of the drain, so that a complete treatment assembly is conveniently provided. The used parts may be adapted to be disposable, to prevent inadvertent re-use for another patient or other known blood-related biohazards.

For recuperating blood from wound drained blood with the filtering device 1, a blood receptacle is connected to the exit port 6. The blood receptacle may be an evacuated blood bag, a blood bag with washing or preserving liquid or any other suitable device. It may also be a blood reinfusion device for direct on-line reinfusion of the blood.

Next, the drain 3 is applied to the wound site in any known appropriate manner, and the drained blood—comprising impurities—is introduced into the filtering device 1 through the connection 3.

The device may be used in the clinical situation, connected to the patient wound-site or independently, i.e. disconnected from a patient, to filter collected wound drained blood.

In the former situation, a fluid-filled drain may simply siphon the wound drained blood under influence of gravity from the wound site to the filtering device when it is placed lower than the wound site, e.g. on the ground next to the patient's bed. The draining may be assisted by aspiration by means of a low vacuum inside the filtering device, e.g. derived from an evacuated blood bag, or derived from a vacuum source connected with the vacuum connection 5, e.g. using a vacuum pressure of −30 cm $H_2O$.

In the latter situation, the filtering may be assisted by means of a deeper vacuum, which is preferably less than −200 mm Hg, e.g. −120 mm Hg.

Upon introduction into the filtering device 1, emboli and/or relatively large particulate impurities are removed from the wound drained blood by the first filter 7 and smaller particles, including red blood cells are passed through the first filter 7. Via the baffle 9 the blood is supplied to the second filter 8.

The second filter 8 serves to retain the red blood cells and to filter out smaller impurities left in the blood after the first filtering step. The residue of the second filter 8 is collected at the exit port 6 and the filtrate is received in the reservoir 10 and is considered a waste product of the present process.

As is clearly visible, in the embodiment of FIGS. 1 and 2, the first filter 7 has a top (upstream) surface, which is convex, tapering in the upstream direction. This shape causes the incoming drained blood to flow off to the sides of the filter 7 where residue may be amassed, leaving the central portion of the filter surface essentially clear. Thus, this feature prevents clogging of the first filter 7 to a large degree and allows to use a smaller pore size than the customary 40 μm, e.g. down to about 15 μm, to remove smaller debris if so desired. However, a larger pore size than 40 μm allows faster filtering and reduces the need for applying a pressure difference across the filter, such as by means of a vacuum.

A concave-shaped first filter 7 can also be used. This has the effect that the residue is amassed at or near the bottom of the filter, where it may act as an additional filter material which may reduce the filtering speed and -yield, but at the same time may cause the filtrate to be of a higher quality, i.e. containing less impurities.

Figure 3:
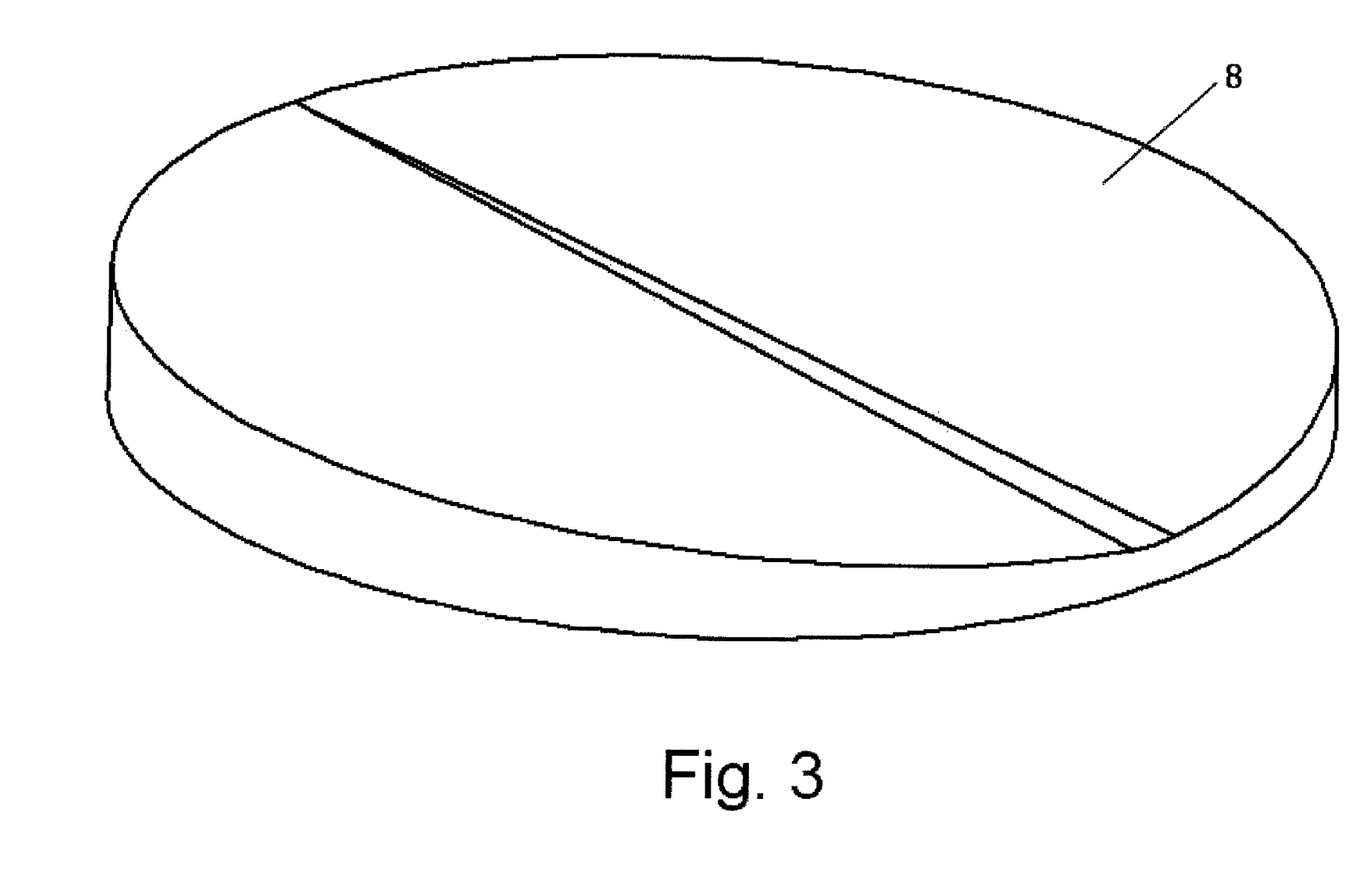
FIG. 3 is a larger scale perspective view of a second filter, suitable for use in the filtering device of FIG. 1.

The second filter 8 has a main surface orientation at an angle to the horizontal (FIGS. 1-3). The exit port 6 is located at least near the relatively lowest point or edge of the second filter. This causes the blood to flow across the surface of the second filter 8 towards the exit port 6 under the influence of gravity.

The baffle 9 is arranged at an angle to the horizontal and is provided with three apertures near its lower side (FIG. 2). Thus, the baffle 9 serves to direct the blood to the relatively high sides of the second filter 8 to use the maximum path length for filtering.

The overall selectivity of the second filter 8 is determined by its pore size and the effectively filtered quantity is determined to a certain extent by the filtration time.

The duration of the second filtering step is mainly determined by the flow velocity of the blood across the filter surface of a given size. The flow velocity is inter alia determined by the combination of the angle of the filter with respect to the horizontal, the viscosity of the blood and the roughness or smoothness of the upstream surface of the filter 8. The filtration time may be adapted by opening or closing of the valve 6A.

A suitable filter may have an upstream surface which is, apart from the pores, substantially smooth at a micron size scale, preferably at a sub-micron size scale, e.g. such that the surface has a shiny appearance. The filter may have a hard surface, or may also be a woven mesh filter of smooth filaments, e.g. of the type used for filtering beer. Such a smooth filter surface appears to leave red blood cells substantially intact and to reduce the probability of tangling and trapping of red blood cells in the filter material.

An angle of the main surface orientation of the second filter 8 to the horizontal of more than about 15 degrees usually provides insufficient filtration with such a smooth filter, as the blood then flows down to the exit port 6 essentially unfiltered. An angle of about 6 degrees provides proper filtering of impurities, yet may leave fluid, such as washing fluid or irrigation fluid in the residue. An angle of about 3 degrees (FIGS. 1-3) provides effective filtering of both impurities and of fluids.

To direct the blood which is being filtered by the second filter 8 more efficiently to the exit port 6, the upstream surface of the filter is provided with guiding features, such as folds or side facets which are applied to or extend from the main surface as indicated more clearly in FIG. 3. Similarly, the filter surface may be provided with structures to spread the blood to be filtered more evenly across the filter surface, if so desired.

The second filter 8 may also have a conical or generally convex shape (not shown). A sloping intersection of (the shape of) the second filter 8 with the wall of the housing 2 may provide a channel for directing the red blood cells towards the exit port 6. The baffle 9 may be formed to supply the blood at the top or apex of the second filter 8. Similar to a concave filter, the top angle of a conical second filter may be on the order of about 3-15 degrees whereas a spherical filter may range from essentially flat to approximately a half-sphere. The channel along the intersection may have an angle to the horizontal of up to about 15 degrees, e.g. 6 degrees or 3 degrees, for efficient filtering and guiding of the blood cells to an exit port.

Washing liquid, e.g. a saline solution or Ringer's solution with a bolus dose of an anticoagulation drug such as heparin, may be introduced in the device to flush the filters 7, 8 and/or the intermediate baffle 9 and/or to assist the blood cells to collect at the bottom of the second filter 8.

The blood and the washing liquid may be introduced in the filtering device 1 relatively close to the centre of the first filter 7. This arrangement causes the fluids to flush and keep clear the first filter 7 to reduce clogging thereof and to retrieve as many red blood cells as possible.

When a washing fluid is used, some of it may be collected in the blood receptacle and not be filtered out. However, with the proper choice of washing fluid, e.g. a saline solution or a Ringer's solution, the quality of the red blood cells is essentially unaffected.

Figure 4:
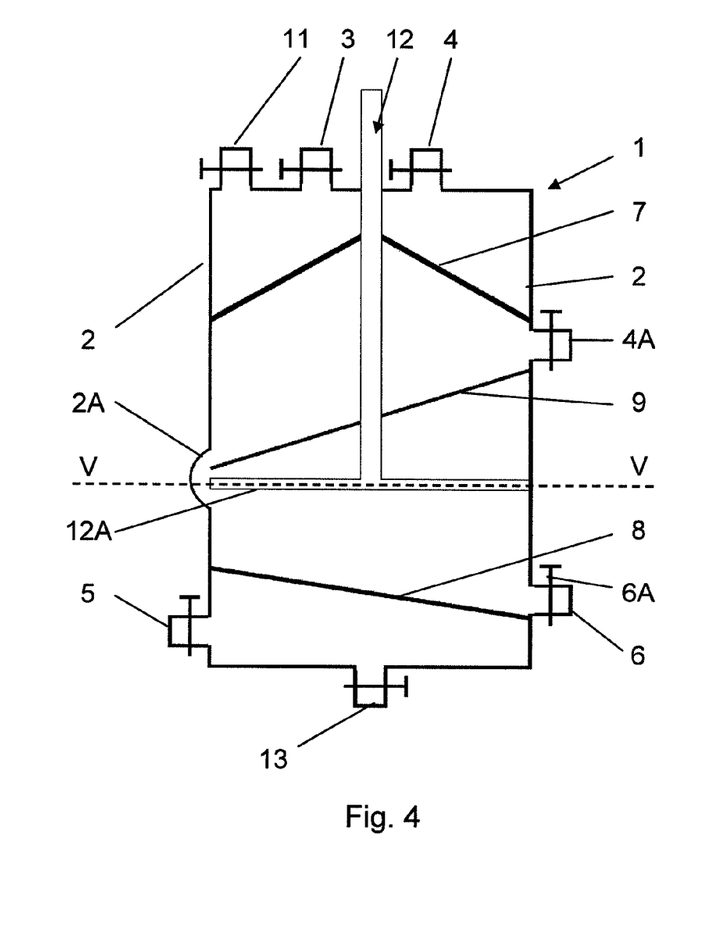
FIG. 4 is a cross sectional view of a second embodiment of a blood filtering device.
Figure 5:
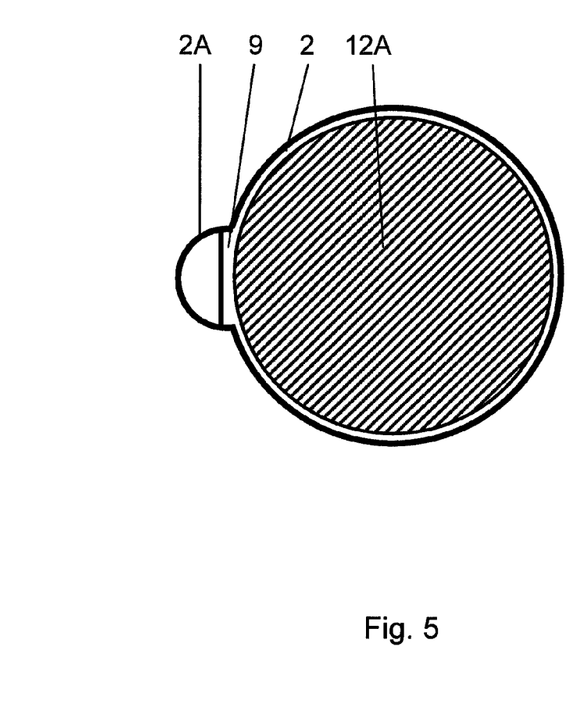
FIG. 5 is a cross sectional view of the blood filtering device according to FIG. 4 perpendicular along the line V-V to the view of FIG. 4.
Figure 6:
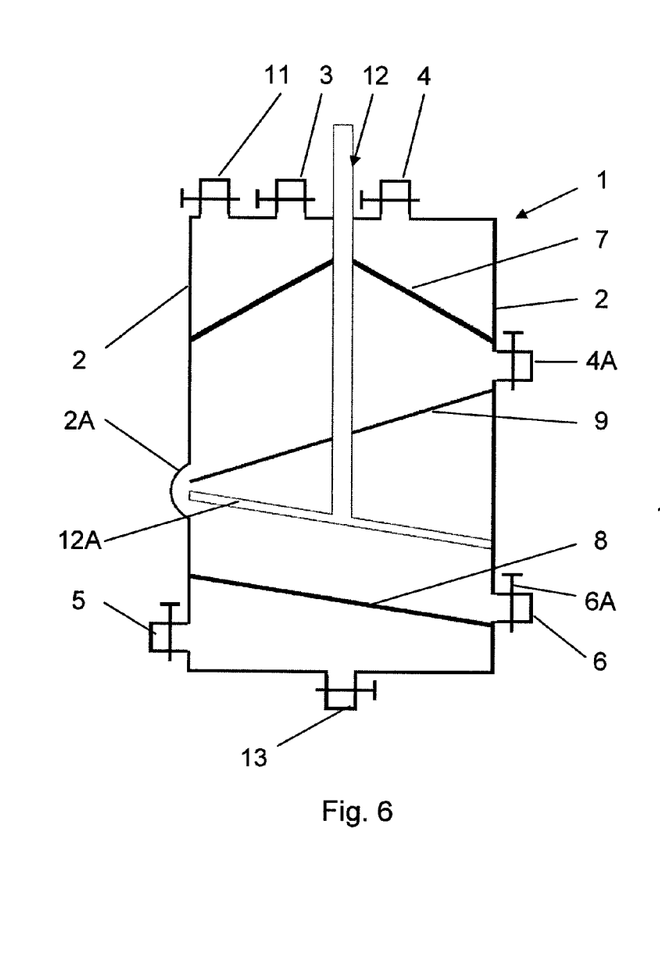
FIGS. 6-10 are cross sectional views of further embodiments of a blood filtering device.
Figure 7:
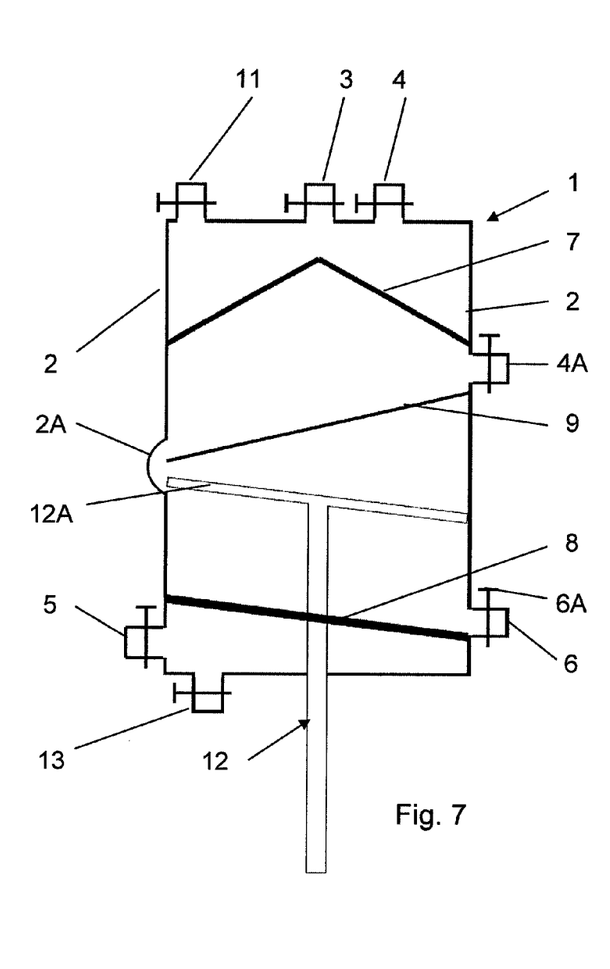

FIGS. 4 and 5 show two cross sections perpendicular to each other of another embodiment of a blood filtering device. FIGS. 6 and 7 show variations of the embodiment of FIG. 4.

In these and subsequent Figures, parts having the same or equivalent functions as those in a previously-discussed embodiment bear the same reference numeral.

In FIGS. 4-7, the housing 2 is provided with a bypass channel 2A, which here is formed as a bulge in the wall of the housing 2 (most clearly shown in FIG. 5) but which may also be formed as a separate conduit such as a pipe or a hose, possibly provided with a valve. The filter device 1 is further provided with an additional closable connection 4A for one or more sources of washing fluid, with a plunger 12 having a plunger head 12A and with a closable exit 13 for filtrate of the second filter 8. The baffle 9 may provide a single exit in the bypass channel 2A such that fluid flowing over the baffle 9 bypasses the plunger head 12A, as indicated in FIG. 5.

The plunger head 12A fits against the inside of the housing wall 2 (for clarity, the wall 2 and the plunger head 12A are drawn separated in FIG. 5). The plunger may be provided with a flexible or resilient rim for fitting the plunger head 12A snugly and providing an essentially fluid tight seal. In the embodiment of FIGS. 6 and 7, the plunger head 12A is formed substantially matching the upper surface of the second filter 8. In the embodiment of FIGS. 4-6 (7) the plunger 12 protrudes through an opening in the first (second) filter.

The rim of the opening may be provided with an upstanding rim, to prevent leaking or spilling blood past the filter surface.

Upon pressing or pulling (FIG. 7) the plunger downward past the exit of the bypass channel 2A, the plunger head 12A will fit against the housing wall 2 over the entire circumference and thus essentially close off the lower part of the housing. Any, possibly all, ports extending into or out of the housing 2, in particular under or downstream of the plunger head 12 may be closable for closing-off an interior volume of the housing 2, thus allowing to apply fluid pressure by the plunger. Thus, the plunger 12 is adapted for applying fluid and mechanical pressure to the filtrate of the first filtering stage and thus it is adapted for applying or increasing the filtering pressure across the second filter 8. Thus, the second filtering step may be assisted. The second filtering step may be executed with or without additional vacuum suction through connector 5.

The plunger 12 may be operated by any hydraulic, pneumatic or mechanical means. Manual operation is also conceivable. The plunger may also be integrated with the baffle 9 (not shown).

For washing filtrate of the first filter off of the baffle 9 and/or for additional rinsing of the (pressed) filtrate, washing fluid may be applied from connections 4 and/or 4A. Filtrate from the second filter 8 may be drained by exit port 13, which may be assisted by providing the housing 2 with a sloping bottom.

Figure 8:
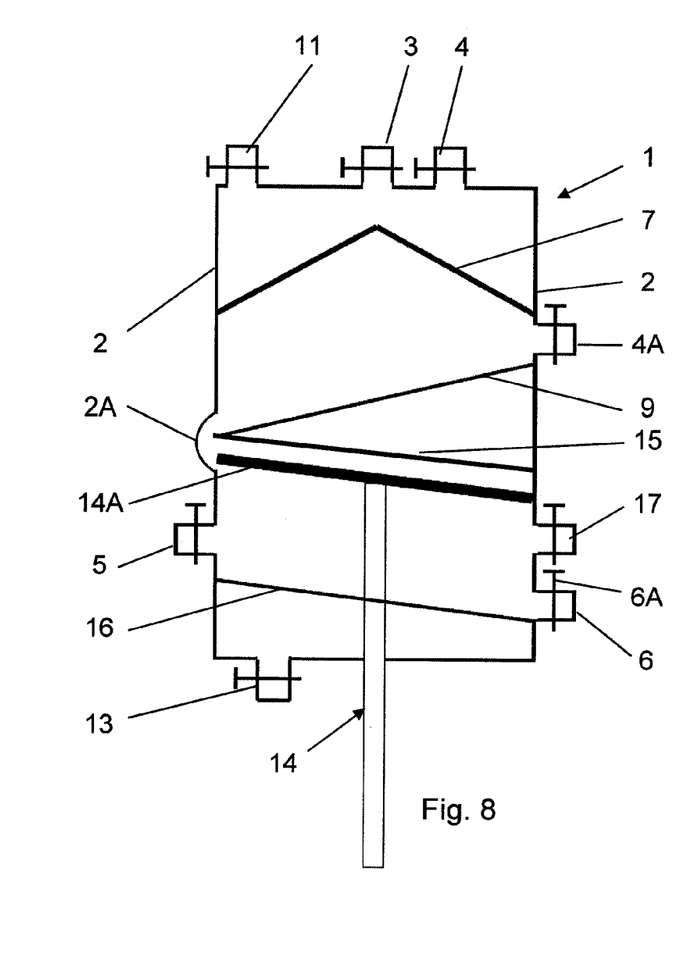
Figure 9:
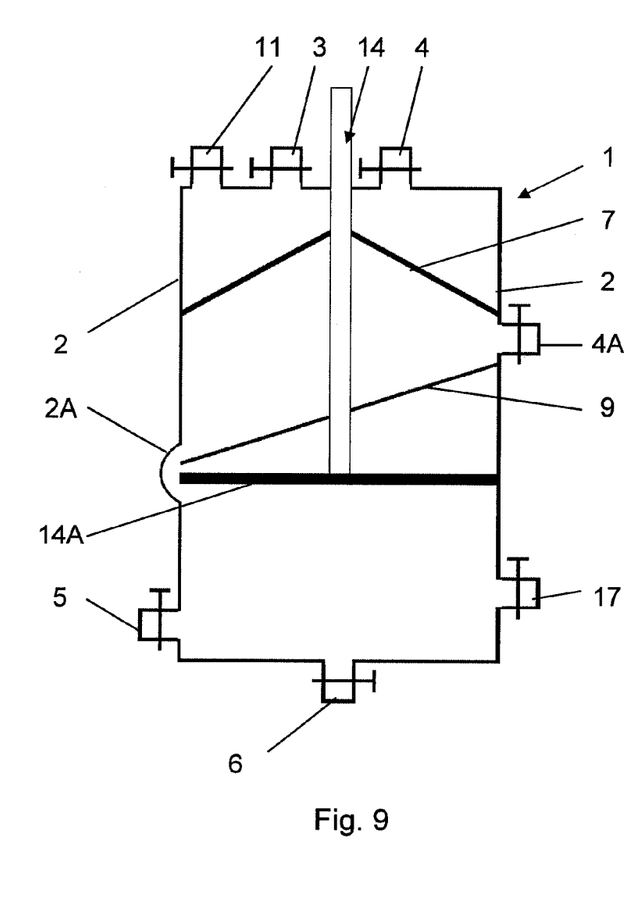
Figure 10:
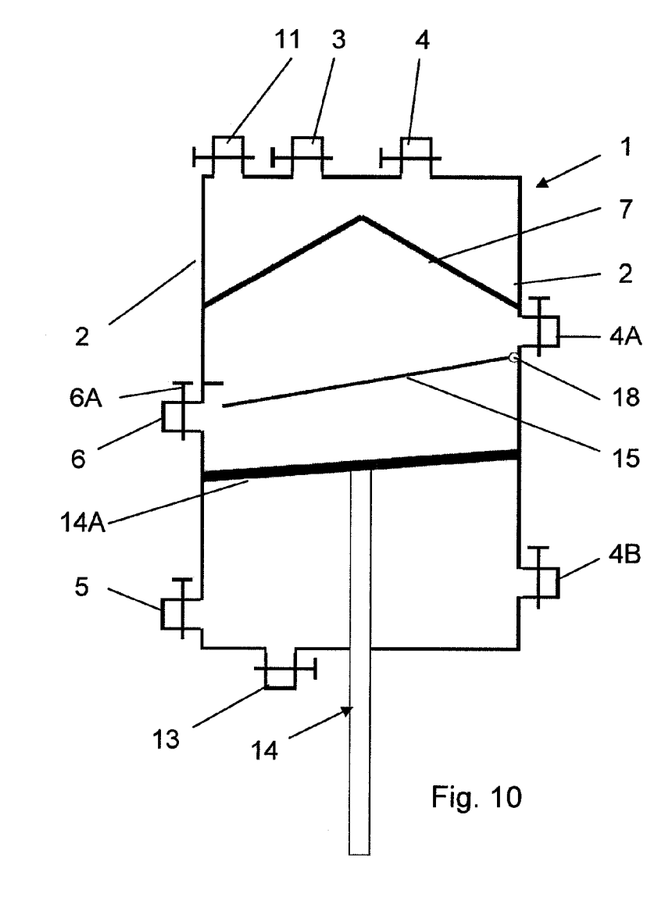

In the embodiments of FIGS. 8-10, a plunger 14 is provided, of which the plunger head 14A is provided with a filter material such that it acts as the second filter.

In the embodiment of FIG. 8, the filter device 1 is provided with an additional upper surface 15, with a lower surface 16, and with an additional port 17. The upper surface 15 may be part of the baffle 9, e.g. be the bottom thereof. The lower surface 16 may be the bottom of the filter housing 2. Alternatively, the lower surface 16 is the second filter 8.

In the embodiment of FIG. 8, the filtrate of the first filter 7 may be supplied onto the top of the plunger head filter 14A. In this case, the filtering proceeds as described above, now through the filtering plunger head 14A instead of through the filter 8. The plunger 14 may be pressed upwards against surface 15 to increase the filtering pressure across the second filter, i.e. the filtering plunger head 14A. The retained blood cells may be recuperated through ports 6 or 17.

Alternatively, the filtrate of the first filter may be fed past the plunger head 14A onto the lower surface 16. The plunger 14 may be forced downwards to apply pressure onto the filtrate of the first filter 7 on the surface 16 and squeeze the fine particles thereout. This process may be repeated with and/or assisted by relatively large amounts of washing fluid and/or an essentially one-way filtering process, such as by selecting an appropriate, e.g. polar, filter material. In this process the filtering flow in the second stage is upwards. The retained blood cells, being underneath the second filter in the plunger head 14A but effectively upstream thereof, may be recuperated through the port 6.

In case the lower surface 16 is the second filter 8, the filtrate may be pressed sandwiched between two filters 8 and 14A, increasing the filtering surface. Thus the filtering and washing efficiency of the device may be further increased. Then the vacuum port 5 may be placed downstream of the second filter 8. The device 1 may also comprise a plurality of vacuum connections, allowing to optimize the configuration of the device 1 for a particular method of its use.

The embodiment of FIG. 9 is a simplified form of that of FIG. 8, lacking the surface 15 and with the surface 16 being the bottom of the housing 1. The plunger 14 is oriented upwards. This embodiment is suitable for the second method of operation described with respect to FIG. 8.

Figure 11A:
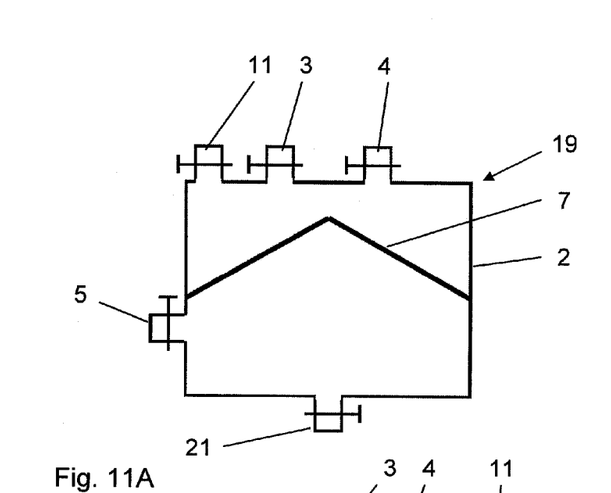
FIGS. 11A and 11B are cross sectional views of an embodiment of a blood filtering device having the first and second filters comprised in two different housings.
Figure 11B:
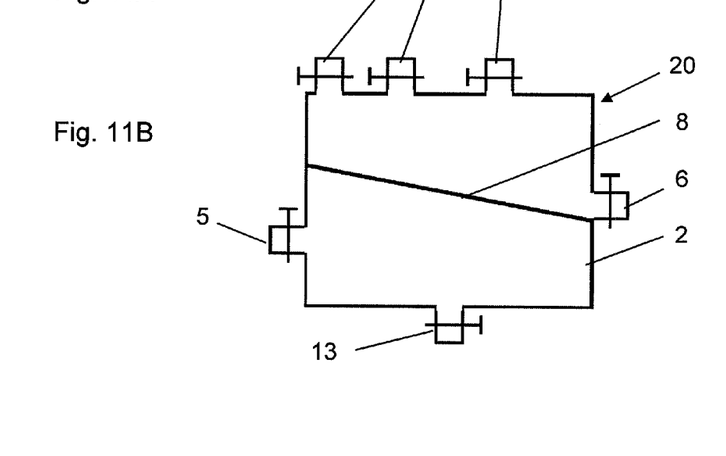

In the embodiment of FIG. 10, the baffle 9 is provided with hinging means 18, e.g. a flexible part or a hinge, such that the baffle 9 may be closed and the flow of filtrate from the first filter 7 to the second filter may be halted. At the same time, the baffle 9 may serve as a surface against which the plunger 14 may be pressed for increasing the filtering pressure across its filtering plunger head 14A. FIGS. 11A and 11B show the first and second filter 7 and 8, respectively, being provided as separate devices, 19 and 20, respectively, i.e. both filters are provided in different housings 2. Both filtering devices 19 and 20 are provided with an individual vacuum connector 5. The first filtering device 19 comprises an output port 21 for the filtrate. Another output port (not shown) may be provided for the residue of the first filter 7. The output port 21 may be connected directly or indirectly, e.g. by means of a hose, a pipe or a different type of conduit, to the entrance port 3 of the second filtering device 20 to make up a complete blood filtering device.

The individual housings 2 allow to provide one or more valves between the devices 19 and 20 and may allow a deeper vacuum for expediting the second filtering step, whereas the wound site is not exposed to a deeper vacuum. The differential pressure across the second filter may be increased to just below damaging the red blood cells, which is believed to occur at about −5000 mmHg, possibly depending on the filter material. The housings 2 need not be permanent attached to each other and may be stand-alone devices.

Figure 12:
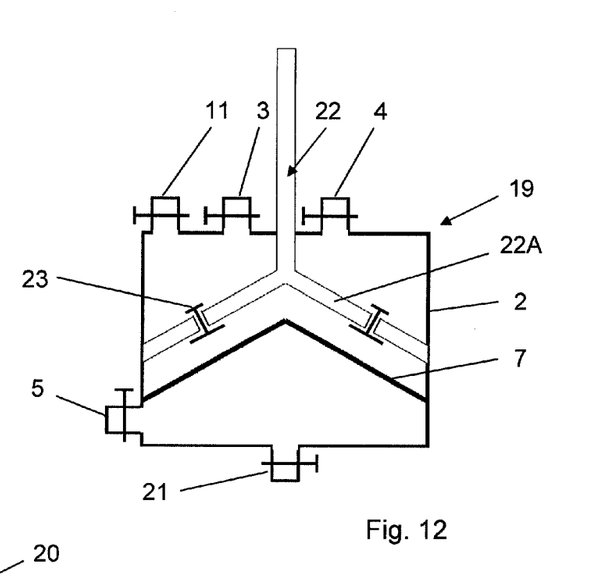
FIG. 12 is a cross sectional view of an embodiment of a housing with a first filter and a plunger.

When using different housings 2, a plunger arrangement, such as in FIGS. 4-10, may be provided in one or each housing 2. E.g., FIG. 12 indicates a possible plunger arrangement for the first filter 7. In FIG. 12, the first filter device 19 is provided with a plunger 22 with a formed plunger head 22A. The plunger head is provided with one or more valves 23 allowing blood and washing fluid to pass through the plunger head 22A and allowing it to be raised relatively easily. Upon lowering the plunger 22 the valves 23 are pressed shut, allowing pressure build-up against the filter 7. Instead of valves 23 the plunger head 22A may be provided with one or more flexible membranes and/or with a flexible rim or skirt around (a portion of) its perimeter.

One or more plungers (12, 14, 22) may be used to provide a reduced pressure suction to a more upstream part of the device, potentially obviating other vacuum sources.

It is believed that, without wishing to be bound to any specific theory, a reduced temperature reduces the ability and/or likelihood of the red blood cells to flex and to pass through smaller openings than the diameter of a red blood cell at rest, and even might prevent a red blood cell from passing through an opening which is slightly larger than its diameter. The natural reduction from body temperature to ambient room temperature, i.e. from about 37 degrees Celsius to about 20 degrees Celsius, already causes a substantial increase in the efficiency of the filter, as less blood cells pass therethrough.

A filtering device according to the present disclosure may be used for several hours on end, during which the filtered blood may be left in the device, on the second filter or the blood may be collected in a blood receptacle.

The residue of the second filter, comprising the recuperated blood cells may also comprise white blood cells or leukocytes having the same size as the red blood cells. These leukocytes should preferably be removed before reinfusion of the blood, which can efficiently be done by passing the autologous blood through a commercial leukocyte filter (Pall filter).

Due to its relative simplicity, and due to the fact that no complicated additional apparatus such as pumps are required for the operation of the present filtering device, the device may be produced and/or used relatively cost-effectively. This makes the filtering device very well suited for use in poorer and/or less-developed countries, where the risks of infections or diseases, particularly AIDS, from a homologous blood transfusion are much higher than in more-developed countries.

The disclosure is not restricted to the above described embodiments which can be varied in a number of ways within the scope of the claims. For instance, additional filters or devices may be used or added for recuperating other blood products, such as intact platelets or blood plasma, from the filtrate of the second filter. As with the first and second filters, additional filters or devices may also be provided in different housings.

Further, one or more of the filters may be made from a filtering material which does not solely function on a size cut-off, but which also provides a filtering action based on biophysical or biochemical properties, such as (a-)polarity of the particles to be filtered out or retained.

Further, the directing function of the baffle may also be fulfilled by a funnel, a conduit or by generally shaping the housing 2 appropriately, e.g. providing it with a sloping side and arranging the first and second filters 7, 8, offset from another.

The functionality of a plunger for applying mechanical and/or fluid pressure to the substance to be filtered for increasing the filtering pressure may also be provided with a rotatable screw, compressing fluid between the screw-blade and the filter, by providing the housing 2 with a deformable portion, such as a bellows, providing the device with a flexible membrane etc. Also, a plunger head need not be connected to a plunger rod, but may be a separate device inside the housing, e.g. an electro-magnetically movable disc.

In case of a sufficiently high filtering efficiency, e.g. due to the filter pore size, vacuum pressure or to mechanical pressure, the angle of a filter may be chosen steeper than 15 degrees to the horizontal for faster guiding the residue to an exit port.

In addition, details and/or elements shown with respect to one embodiment may be combined with those of other embodiments to provide further modifications of a blood filtering device, a kit and/or an assembly within the scope of the appended claims.

Unless explicitly stated otherwise or clearly evident from the text, references to directions such as "up" or "down" refer to the orientation of the embodiments as shown in the Figures and are for explanatory purposes only. Such references should not be taken literally or limiting.

The invention claimed is:

1. A blood filtering device for the recuperation of blood from wound drained blood, comprising
   an entrance port for the blood,
   a first filter,
   a second filter,
   wherein the first filter is arranged upstream of the second filter,
   the first filter being adapted for removing emboli and/or large particulate matter from the blood received through the entrance port, and for allowing red blood cells to pass,
   the second filter adapted for retaining red blood cells, and
   an exit port arranged between the first and second filter, being downstream of the first filter and upstream of the second filter, and wherein
   the second filter has a pore size in the range of about 1-10 µm.

2. The blood filtering device according to claim 1, wherein the pore size of the second filter is in the range of about 2-8 µm.

3. The blood filtering device according to claim 1, wherein the first filter has an upstream surface which is generally convex or concave in the upstream direction.

4. The blood filtering device according to claim 3, wherein the first filter has a pore size of about 15 µm.

5. The blood filtering device according to claim 1, wherein the second filter has an upstream surface which is substantially smooth at a micron size scale.

6. The blood filtering device according to claim 1, wherein the second filter has a main surface orientation at an angle to the horizontal, in a range between 0 and 15 degrees and wherein the exit port is located at least near the relatively lowest point or edge of the second filter.

7. The blood filtering device according to claim 1, wherein the device is adapted for supplying the blood to the second filter at least near the relatively highest point or edge of the second filter.

8. The blood filtering device according to claim 1, further provided with means for connecting a relatively low vacuum source to the device.

9. The blood filtering device according to claim 1, further provided with a connector for connecting a source of washing liquid thereto.

10. The blood filtering device according to claim 1, wherein the device is adapted to be disposable after single use.

11. The blood filtering device according to claim 1, wherein the device comprises means for mechanically increasing the filtering pressure across a filter.

12. The blood filtering device according to claim 11, wherein the means for mechanically increasing the filtering pressure across a filter comprising a plunger.

13. The blood filtering device according to claim 12, wherein the plunger comprises a plunger head provided with a filter material.

14. The blood filtering device claim 1 forming part of a kit, the kit further comprising a conduit for draining wound secretions and a blood receptacle, being packed under sterile conditions.

15. The blood filtering device according to claim 1, wherein the second filter is movable with respect to the exit port.

16. The blood filtering device according to claim 1, wherein the second filter has an upstream surface which is substantially smooth at a sub-micron level.

17. An autologous blood transfusion assembly comprising a blood filtering device for the recuperation of blood from wound drained blood, comprising:
   an entrance port for the blood,
   a first filter and
   a second filter,
   wherein the first filter is arranged upstream of the second filter,
   the first filter being adapted for removing emboli and/or large particulate matter from the blood received through the entrance port and for allowing red blood cells to pass,
   the second filter adapted for retaining red blood cells,
   an exit port arranged between the first and second filter, being downstream of the first filter and upstream of the second filter, wherein
   the second filter has a pore size in the range of about 1-10 µm.

18. A method of recuperating blood from wound drained blood, in particular for an autologous blood transfusion, comprising:
- aspirating or collecting wound drained blood of a patient in a conduit,
- filtering the blood from the conduit in a first relatively coarse manner for removing emboli and/or particulate matter from the blood,
- filtering the coarsely filtered blood in a second relatively fine manner for filtering out small impurities and/or liquid from the blood and retaining red blood cells in the residue, said filtering being performed to retain particles having a size in the range of about 1-10 µm and to remove smaller particles therefrom,
- collecting the residue of the second-mentioned filtering.

19. The method according to claim 18, wherein the second-mentioned filtering is performed to filter out and retain particles having a size of more than about 2 µm and to remove smaller particles therefrom, and wherein the first-mentioned filtering is performed to filter out particles having a size of more than about 15 µm.

20. The method according to claim 18, wherein a duration of the second-mentioned filtering is determined by setting the second filter at a predetermined main angle to the horizontal and by supplying the blood to the second filter at least near its highest point or edge and allowing the blood to flow down across this filter to an exit thereof.

21. The method according to claim 18, wherein a washing fluid is used to expedite the filtering and/or at least assist in collecting the blood cells.

* * * * *